(12) United States Patent
Malec et al.

(10) Patent No.: US 11,114,185 B1
(45) Date of Patent: Sep. 7, 2021

(54) METHOD AND APPARATUS FOR DEFINING A LEVEL OF ASSURANCE IN A LINK BETWEEN PATIENT RECORDS

(71) Applicant: Change Healthcare Holdings, LLC, Nashville, TN (US)

(72) Inventors: Arien Malec, Oakland, CA (US); Chad Bonner, San Francisco, CA (US); Peter Bernhardt, Albany, CA (US); David P. McCallie, Jr., Stilwell, KS (US)

(73) Assignee: CHANGE HEALTHCARE HOLDINGS, LLC, Nashville, TN (US)

( * ) Notice: Subject to any disclaimer, the term of this patent is extended or adjusted under 35 U.S.C. 154(b) by 595 days.

(21) Appl. No.: 14/450,883

(22) Filed: Aug. 4, 2014

Related U.S. Application Data

(63) Continuation of application No. 13/971,529, filed on Aug. 20, 2013, now abandoned.

(51) Int. Cl.
*G16H 10/60* (2018.01)
*G16H 15/00* (2018.01)

(52) U.S. Cl.
CPC .................................. *G16H 10/60* (2018.01)

(58) Field of Classification Search
CPC ............................ G06F 19/322; G06Q 50/24
USPC ........................................................ 705/2, 3
See application file for complete search history.

(56) References Cited

U.S. PATENT DOCUMENTS

| | | | |
|---|---|---|---|
| 5,664,109 A * | 9/1997 | Johnson | G06Q 40/08 705/2 |
| 5,991,758 A | 11/1999 | Ellard | |
| 5,999,937 A | 12/1999 | Ellard | |
| 6,397,224 B1 | 5/2002 | Zubeldia et al. | |
| 6,496,838 B1 | 12/2002 | Zamora-McKelvy et al. | |

(Continued)

FOREIGN PATENT DOCUMENTS

| | | | |
|---|---|---|---|
| CN | 102314478 A | 1/2012 | |
| CN | 103310398 A | 9/2013 | |
| WO | WO-2011042838 A1 * | 4/2011 | ............. G16H 10/60 |

OTHER PUBLICATIONS

St. Sauver, Jennifer L., et al. "Use of a medical records linkage system to enumerate a dynamic population overtime: the Rochester epidemiology project." American journal of epidemiology 173.9 (2011): 1059-1068. (Year: 2011).*

*Primary Examiner* — Elaine Gort
*Assistant Examiner* — Constantine B Siozopoulos
(74) *Attorney, Agent, or Firm* — Myers Bigel, P.A

(57) ABSTRACT

A method, computing device and computer program product are provided to define a level of assurance in one or more links between patient records that relate to the same person based upon external information. In the context of a method, one or more links are identified between a patient record associated with a person and pre-existing patient records. Each pre-existing patient record has a plurality of demographic attributes associated with a patient. The method identifies one or more links based upon an analysis of the demographic attributes of the person and the respective patients associated with the pre-existing patient records. The method receives external information regarding a relationship between the person and the respective patients associated with the pre-existing patient records or regarding confirmation of an identity of the person. The method also defines a level of assurance in the respective one or more links based upon the external information.

18 Claims, 11 Drawing Sheets

(56) References Cited

U.S. PATENT DOCUMENTS

| | | |
|---|---|---|
| 6,523,019 B1 | 2/2003 | Borthwick |
| 6,912,549 B2 | 6/2005 | Rotter et al. |
| 6,922,695 B2 | 7/2005 | Skufca et al. |
| 6,978,268 B2 | 12/2005 | Thomas et al. |
| 6,988,075 B1 | 1/2006 | Hacker |
| 6,996,565 B2 | 2/2006 | Skufca et al. |
| 7,167,858 B2 | 1/2007 | Naeymi-Rad et al. |
| 7,318,059 B2 | 1/2008 | Thomas et al. |
| 7,376,677 B2 | 5/2008 | Ober et al. |
| 7,440,094 B2 | 10/2008 | Yoo |
| 7,509,264 B2 | 3/2009 | Hasan et al. |
| 7,523,505 B2 | 4/2009 | Menschik et al. |
| 7,526,486 B2 | 4/2009 | Cushman, II et al. |
| 7,620,647 B2 | 11/2009 | Stephens et al. |
| 7,627,550 B1 | 12/2009 | Adams et al. |
| 7,685,093 B1 | 3/2010 | Adams et al. |
| 7,698,154 B2 | 4/2010 | Marchosky |
| 7,698,268 B1 | 4/2010 | Adams et al. |
| 7,707,047 B2 | 4/2010 | Hasan et al. |
| 7,725,331 B2 | 5/2010 | Schurenberg et al. |
| 7,801,878 B2 | 9/2010 | Hayes et al. |
| 7,856,366 B2 | 12/2010 | Dettinger et al. |
| 7,941,328 B2 | 5/2011 | Castille |
| 8,090,590 B2 | 1/2012 | Fotsch et al. |
| 8,095,386 B2 | 1/2012 | Lassetter et al. |
| 8,108,311 B2 | 1/2012 | Herlitz |
| 8,126,740 B2 | 2/2012 | Busch |
| 8,135,679 B2 | 3/2012 | Bayliss |
| 8,165,899 B2 | 4/2012 | Yeh et al. |
| 8,200,509 B2 | 6/2012 | Kenedy et al. |
| 8,249,895 B2 | 8/2012 | Faulkner et al. |
| 8,321,383 B2 | 11/2012 | Schumacher et al. |
| 8,321,393 B2 | 11/2012 | Adams et al. |
| 8,332,366 B2 | 12/2012 | Schumacher et al. |
| 8,356,009 B2 | 1/2013 | Ellard et al. |
| 8,359,339 B2 | 1/2013 | Adams et al. |
| 8,370,355 B2 | 2/2013 | Harger et al. |
| 8,370,366 B2 | 2/2013 | Adams et al. |
| 8,417,702 B2 | 4/2013 | Harger et al. |
| 8,423,382 B2 | 4/2013 | Dettinger et al. |
| 8,423,385 B2 | 4/2013 | Radoccia et al. |
| 8,423,514 B2 | 4/2013 | Goldenberg et al. |
| 8,429,220 B2 | 4/2013 | Wilkinson et al. |
| 8,438,182 B2 | 5/2013 | Gillam et al. |
| 8,452,619 B2 | 5/2013 | Kenedy et al. |
| 8,510,129 B2 | 8/2013 | Morris |
| 8,527,295 B2 | 9/2013 | D'Ambrosia |
| 8,620,930 B2 | 12/2013 | Gulhane et al. |
| 8,621,244 B1 | 12/2013 | Rembert et al. |
| 2004/0102998 A1 | 5/2004 | Bao et al. |
| 2005/0005168 A1* | 1/2005 | Dick .................. G06F 21/6245 726/4 |
| 2005/0222876 A1 | 10/2005 | Iwayama et al. |
| 2006/0080312 A1 | 4/2006 | Friedlander et al. |
| 2007/0299697 A1* | 12/2007 | Friedlander ........... G06F 19/322 705/3 |
| 2009/0024417 A1 | 1/2009 | Marks et al. |
| 2009/0089317 A1 | 4/2009 | Ford et al. |
| 2009/0150451 A1 | 6/2009 | Gejdos et al. |
| 2009/0198686 A1 | 8/2009 | Cushman, II et al. |
| 2009/0326982 A1 | 12/2009 | Deobhakta et al. |
| 2010/0114877 A1 | 5/2010 | Adams et al. |
| 2010/0131298 A1 | 5/2010 | Buttner et al. |
| 2010/0175024 A1* | 7/2010 | Schumacher ..... G06F 17/30489 715/810 |
| 2010/0179834 A1 | 7/2010 | Wager |
| 2011/0010401 A1 | 1/2011 | Adams et al. |
| 2011/0106564 A1 | 5/2011 | Hachmeister et al. |
| 2011/0191349 A1 | 8/2011 | Ford et al. |
| 2011/0246230 A1 | 10/2011 | Sie et al. |
| 2011/0246234 A1 | 10/2011 | Irwin et al. |
| 2011/0246237 A1 | 10/2011 | Vdovjak |
| 2011/0246238 A1 | 10/2011 | Vdovjak |
| 2011/0282688 A1 | 11/2011 | Raggousis |
| 2011/0305376 A1* | 12/2011 | Neff ..................... G06F 19/327 382/128 |
| 2012/0010904 A1 | 1/2012 | Buck et al. |
| 2012/0059668 A1 | 3/2012 | Baldock et al. |
| 2012/0072237 A1 | 3/2012 | Campbell et al. |
| 2012/0078663 A1 | 3/2012 | Lorsch |
| 2012/0095923 A1 | 4/2012 | Herlitz |
| 2012/0109685 A1 | 5/2012 | Carter et al. |
| 2012/0150887 A1 | 6/2012 | Clark et al. |
| 2012/0203576 A1* | 8/2012 | Bucur .................... G06Q 10/06 705/3 |
| 2012/0245954 A1 | 9/2012 | Klotz et al. |
| 2012/0246741 A1 | 9/2012 | Klotz et al. |
| 2012/0284056 A1 | 11/2012 | Hofstetter |
| 2013/0080192 A1 | 3/2013 | Bucur et al. |
| 2013/0095459 A1* | 4/2013 | Tran ..................... A61B 5/6816 434/247 |
| 2013/0179186 A1 | 7/2013 | Birtwhistle et al. |
| 2013/0204880 A1 | 8/2013 | Lesiecki et al. |
| 2013/0262141 A1 | 10/2013 | Crockett |
| 2013/0290032 A1 | 10/2013 | Netsch et al. |
| 2014/0278542 A1 | 9/2014 | Fernandez |

\* cited by examiner

METHOD AND APPARATUS FOR DEFINING A LEVEL OF ASSURANCE IN A LINK BETWEEN PATIENT RECORDS

CROSS REFERENCE TO RELATED APPLICATION

This application is a continuation of and claims priority to U.S. application Ser. No. 13/971,529, filed on Aug. 20, 2013, the entire contents of which are hereby incorporated by reference.

TECHNOLOGICAL FIELD

An example embodiment of the present invention relates generally to the establishment of links between patient records and, more particularly, to the definition of a level of assurance in a link between patient records.

BACKGROUND

Patient records are being increasingly maintained in an electronic format so as to facilitate the identification, retrieval and sharing of the patient records while correspondingly reducing the need for physical records. A patient record may be maintained by a healthcare facility and may include information regarding a patient, such as various demographic attributes of the patient, e.g., name, address, date of birth, etc., and encounters of the patient with the healthcare facility. A patient record may also include or be associated with other information, such as one or more documents related to the patient's healthcare including, for example, the physician's notes, lab results and/or images of the patient, e.g., x-rays, magnetic resonance imaging (MRI) images, computer aided tomography (CAT) scans, etc.

Some persons may visit multiple healthcare facilities over the course of time. These healthcare facilities may be owned and operated by different healthcare organizations. Each healthcare facility may maintain a patient record, but the patient records maintained by the different healthcare facilities may be independent of one another since the different healthcare organizations that own and operate the healthcare facilities may not share patient records or otherwise cooperate to maintain a common patient record.

In order to have a more complete and comprehensive understanding of a patient's health, a physician or other healthcare practitioner may wish to have access to all of the patient records, regardless of the healthcare facility that created and maintains the patient records. However, in an instance in which a person has visited multiple healthcare facilities that are owned or operated by different healthcare organizations and unless the person has collected and provides a physician or other healthcare practitioner with all of their patient records from the various healthcare facilities that they have visited, the physician or other healthcare practitioner may have difficulty accessing or be unable to access the plurality of patient records maintained for the person by the various healthcare facilities. This difficulty may be exacerbated by the assignment of a different, unique patient identifier to the patient by at least some of the healthcare facilities since a healthcare practitioner may be unaware of the patient identifier associated with the patient by other healthcare facilities and, as such, may have difficulty identifying the patient to the other healthcare facilities.

As such, a healthcare practitioner may find it difficult to readily access all of the patient records created and stored by the various healthcare facilities that have treated the person in the past. Even in instances in which patient records maintained by another healthcare facility are accessible, it may be difficult to gauge the reliability with which the patient records have been initially identified to relate to prior health care of the person, that is, it may be difficult to determine if the patient records that are initially identified to relate to prior health care of the person are actually related to the same person or to a different person. Thus, a healthcare practitioner may not have the benefit of the information contained in at least some of the patient records maintained by other healthcare facilities and even if a healthcare practitioner does have access to patient records the level of assurance that the patient records relate to the same patient may be difficult to estimate, thereby potentially reducing the efficiency with which the healthcare practitioner may treat a patient.

BRIEF SUMMARY

A method, computing device and computer program product are provided in accordance with an example embodiment in order to define a level of assurance in one or more links between patient records that relate to the same person. The level of assurance may be defined based, at least in part, upon external information, such as external information provided by the person or by a healthcare practitioner on behalf of the person. In this regard, the patient care setting allows for the receipt of external information from a person which may assist in appropriately defining the level of assurance of the respective links. By defining the level of assurance in each link, the method, computing device and computer program product of an example embodiment may permit different actions to be taken with respect to the patient records based upon the level of assurance in the link to the patient records.

In accordance with one embodiment, a method is provided that includes identifying, with processing circuitry, one or more links between a patient record associated with a person and pre-existing patient records. Each pre-existing patient record has a plurality of demographic attributes associated with a patient. The method of this embodiment identifies one or more links based upon an analysis of the demographic attributes of the person and the respective patients associated with the pre-existing patient records. In response to the identification of one or more links, the method receives external information regarding a relationship between the person and the respective patients associated with the pre-existing patient records or regarding confirmation of an identity of the person. The method also defines a level of assurance in the respective one or more links based upon the external information.

The method of one embodiment may define an initial level of assurance in the respective one or more links in response to identification of the one or more links. In this embodiment, the method may also define the level of assurance by re-defining the initial level of assurance in the respective one or more links based upon the external information. In this regard, the method of one embodiment may re-define the initial level of assurance in an instance in which external information is provided in association with both the patient record associated with the person and a pre-existing patient record linked thereto. The method of one embodiment may also include re-defining the level of assurance in a respective link in response to receipt of further external information following definition of the level of assurance.

The method of one embodiment may receive external information by receiving confirmation or denial from the person as to whether the person is the respective patient associated with a pre-existing patient record. The method may additionally or alternatively receive external information by receiving confirmation of an identity of a person based upon an identification credential. Further, the method may additionally or alternatively receive external information by receiving confirmation of an identity of the person based upon biometric information. In one embodiment, the method may receive external information by receiving external information from a third-party verification service, such that the level of assurance is defined based at least in part upon the external information from the third party verification service.

The external information regarding confirmation of the identity of the person may have an associated authority. In this embodiment, the method may define the level of assurance in the respective one or more links based at least in part upon the authority of the external information regarding confirmation of the identity of the person. The method of one embodiment may also include permitting the external information that is received and upon which the level of assurance is defined to be extended.

The method of one embodiment may define the level of assurance based upon a number of patient care settings that have received equivalent external information regarding a relationship between the person and the respective patients associated with the pre-existing patient records or regarding confirmation of an identity of the person. The method of an example embodiment may define the level of assurance in the respective one or more links based at least in part upon a level of assurance associated with the healthcare facility that receives the external information from the person. In one embodiment, the method may also include permitting different actions to be taken with respect to the pre-existing patient records depending upon the level of assurance in the links to the respective patient records.

Corresponding computing devices and computer program products are also provided according to other embodiments. For example, in one embodiment, a computing device is provided that includes processing circuitry configured to identify one or more links between a patient record associated with a person and pre-existing patient records. Each pre-existing patient record has a plurality of demographic attributes associated with a patient. The processing circuitry of this embodiment is also configured to identify one or more links based upon an analysis of the demographic attributes of the person and the respective patients associated with the pre-existing patient records. In response to the identification of one or more links, the processing circuitry is configured to receive external information regarding a relationship between the person and the respective patients associated with the pre-existing patient records or regarding confirmation of an identity of the person. The processing circuitry is also configured to define a level of assurance in the respective one or more links based upon the external information.

The processing circuitry of one embodiment may be configured to define an initial level of assurance in the respective one or more links in response to identification of the one or more links. In this embodiment, the processing circuitry may also be configured to define the level of assurance by re-defining the initial level of assurance in the respective one or more links based upon the external information. The processing circuitry of one embodiment may be configured to receive external information by receiving confirmation or denial from the person as to whether the person is the respective patient associated with a pre-existing patient record. The processing circuitry may additionally or alternatively be configured to receive external information by receiving confirmation of an identity of a person based upon an identification credential. Further, the processing circuitry may be configured to additionally or alternatively receive external information by receiving confirmation of an identity of the person based upon biometric information.

In another embodiment, a computer program product is provided that includes a non-transitory computer readable storage medium having program code portions stored thereon with the program code portions configured, upon execution, to identify one or more links between a patient record associated with a person and pre-existing patient records. Each pre-existing patient record has a plurality of demographic attributes associated with a patient. The program code portions of this embodiment are also configured to identify one or more links based upon an analysis of the demographic attributes of the person and the respective patients associated with the pre-existing patient records. In response to the identification of one or more links, the program code portions are configured to receive external information regarding a relationship between the person and the respective patients associated with the pre-existing patient records or regarding confirmation of an identity of the person. The program code portions are also configured to define a level of assurance in the respective one or more links based upon the external information.

The program code portions of one embodiment may be configured to define an initial level of assurance in the respective one or more links in response to identification of the one or more links. In this embodiment, the program code portions may also be configured to define the level of assurance by re-defining the initial level of assurance in the respective one or more links based upon the external information. The program code portions of one embodiment may be configured to receive external information by receiving confirmation or denial from the person as to whether the person is the respective patient associated with a pre-existing patient record. The program code portions may additionally or alternatively be configured to receive external information by receiving confirmation of an identity of a person based upon an identification credential. Further, the program code portions may be configured to additionally or alternatively receive external information by receiving confirmation of an identity of the person based upon biometric information.

BRIEF DESCRIPTION OF THE DRAWINGS

Figure 1:
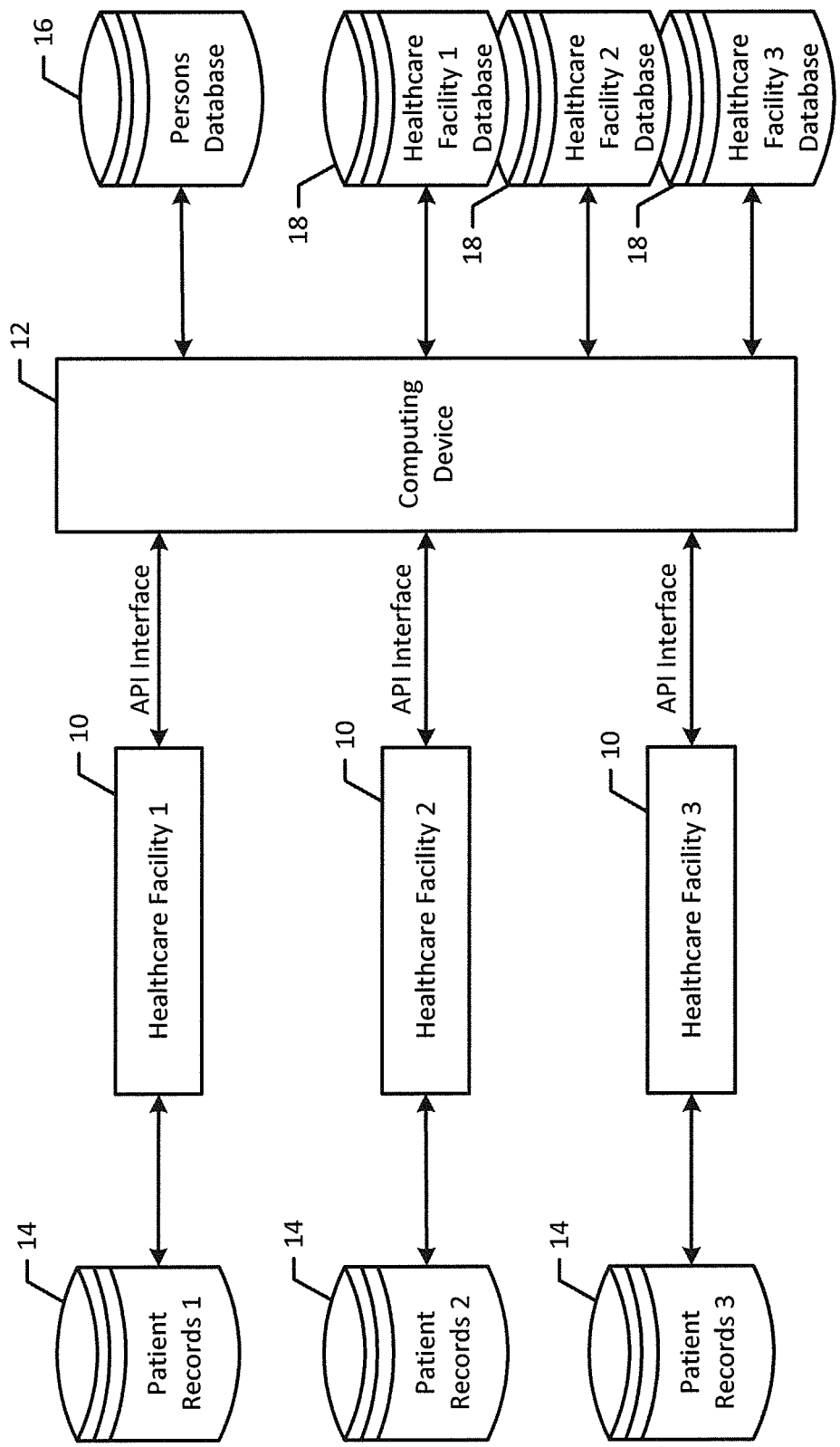
Figure 2:
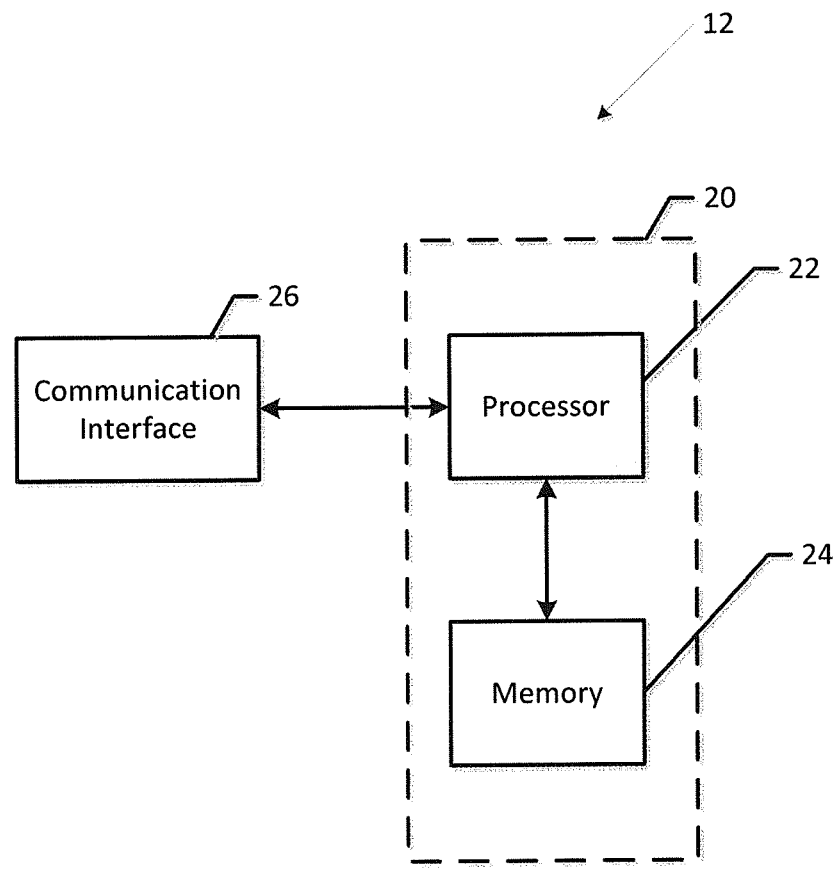
Figure 3:
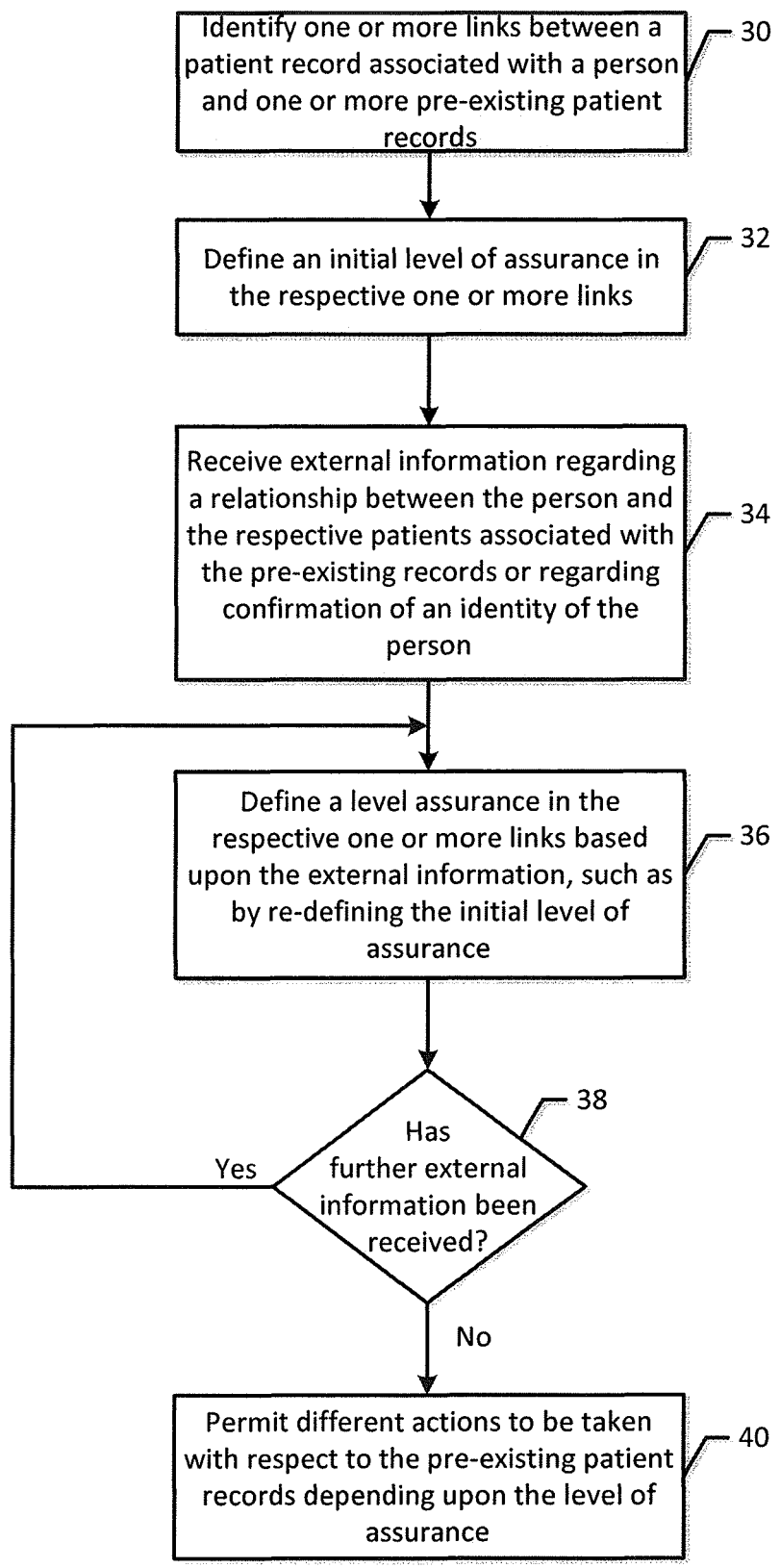

Having thus described certain example embodiments of the invention in general terms, reference will now be made to the accompanying drawings, which are not necessarily drawn to scale, and wherein:

FIG. 1 is a schematic representation of a system for processing patient records that may be specifically configured in accordance with an example embodiment of the present invention;

FIG. 2 is a block diagram of a computing device that may be specifically configured in accordance with an example embodiment of the present invention;

FIG. 3 is a flow chart illustrating operations performed, such as by the computing device of FIG. 2, in conjunction with the definition of a level of assurance in a link between a patient record and a person; and FIGS. 4-11 are sequential representations of the definition of levels of assurance in links between various patient records and a person in accordance with an example embodiment of the present invention.

DETAILED DESCRIPTION

The present invention now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. Further, the apparatus and method of example embodiments of the present invention will be primarily described in conjunction with medical-imaging applications. It should be understood, however, that the apparatus and method may be utilized in conjunction with a variety of other applications, both in the medical industry and outside the medical industry. Like numbers refer to like elements throughout.

A method, computing device and computer program product are provided in accordance with an example embodiment in order to define a level of assurance in one or more links between a patient record associated with a person and pre-existing patient records. In this regard, the method, computing device and computer program product may define the level of assurance in the one or more links based upon external information regarding the relationship between the person and the respective patient associated with the pre-existing patient records or regarding confirmation of an identity of a person. Thus, the confidence with which a healthcare practitioner may rely upon the patient records that have been identified may be informed by the level of assurance defined for the link between the patient records.

Each patient record may include a plurality of demographic attributes associated with the patient, such as the first, middle and last name of the person, the mailing address of the person, the date of birth of the person, etc. Additionally, a patient record may include information describing one or more encounters of a patient with a respective healthcare facility. Patient records may include information regarding a wide variety of encounters including office visits, laboratory tests, hospital admittances, imaging appointments, etc. Some patient records may also include or otherwise be associated with one or more documents. The documents may be associated with one or more of the encounters for which the patient record includes information. The documents may include, for example, laboratory results, notes taken by a physician during an office visit, imaging studies or the like.

The patient records may be created by the healthcare facility that treats the patient. In instances in which the patient has visited a plurality of different healthcare facilities, the patient may have patient records that have been created by each of a plurality of different healthcare providers. Each healthcare facility may store the patient records for the patients that have been treated by the respective healthcare facility in order to memorialize the health care proved to the patient by the respective healthcare facility. As such, the patient records created by a plurality of healthcare facilities for respective patients are not generally stored in a common database, but are, instead, stored in a distributed fashion amongst the plurality of healthcare providers.

Although each healthcare facility may assign a patient identifier for each patient treated by the respective healthcare facility that is unique within the healthcare facility, a patient is not generally assigned a universal patient identifier that uniquely identifies the patient relative to each of the healthcare facilities. In order to facilitate the identification of patient records that are associated with patients who are considered to match a person in question, information regarding the patient records, such as the information regarding the demographic attributes associated with the patient, may be provided by the healthcare facilities to a computing device that may be configured to identify links between a patient record associated with a person and pre-existing patient records that may be associated with the same person and to then determine a level of assurance associated with each link.

While such a system of healthcare facilities may be configured in various manners, FIG. 1 illustrates a block diagram of an example network infrastructure in accordance with example embodiments of the present invention. The example network infrastructure includes a plurality of healthcare facilities 10 in communication with a computing device 12, such as via respective application programming interfaces (APIs) or via a portal application, e.g., a web browser interface. Although three healthcare facilities are depicted in FIG. 1, the system may include any number of healthcare facilities. The healthcare facilities may include any of a variety of facilities visited by a patient that may create and maintain patient records including hospitals, physician practices, laboratories, imaging facilities or the like. As shown in FIG. 1, each healthcare facility may include or otherwise be in communication with a memory device for maintaining a database 14 of patient records for patients who have been treated at the respective healthcare facility.

As described below, the computing device 12 may be configured to receive patient records from the healthcare facilities 10 and to identify links between a patient record associated with a person and pre-existing patient records associated with respective patients (regardless of the healthcare facility that provided the patient records) who are considered to match a person in question, such as a person seeking admittance by one of the healthcare facilities, and to then determine a level of assurance for the respective links. As shown in FIG. 1 and as will also be described below, the computing device may include or otherwise be associated with a persons database 16 for maintaining a record of each person identified by the computing device and a plurality of healthcare facility databases 18, one of which is associated with each healthcare facility that provides patient records to the computing device. The healthcare facility databases may store the patient records provided by the respective healthcare facilities. In one embodiment, the record of a respective person stored by the persons database may include information, such as a link, identifying the patient records stored by the healthcare facility databases that are associated with the person. The persons database and the healthcare facility databases may be portions of a common database or may be distinct databases in various embodiments.

FIG. 2 illustrates a block diagram of a computing device 12 in accordance with some example embodiments. The computing device is capable of functioning in a health information infrastructure and may be embodied by one or more servers, computer workstations, desktop or laptop computers or the like. As described below, the computing device may be configured to implement and/or otherwise support implementation of various example embodiments. However, it should be noted that the components, devices or elements illustrated in and described with respect to FIG. 2 below may not be mandatory and thus some may be omitted in certain embodiments. Additionally, some embodiments may include further or different components, devices or elements beyond those illustrated in and described with respect to FIG. 2.

The computing device 12 may include or otherwise be in communication with processing circuitry 20 that is configurable to perform actions in accordance with one or more example embodiments disclosed herein. In this regard, the processing circuitry may be configured to perform and/or control performance of one or more functionalities of the computing device in accordance with various example embodiments, and thus may provide means for performing functionalities of the computing device. The processing circuitry may be configured to perform data processing, application execution and/or other processing and management services according to one or more example embodiments.

In some example embodiments, the processing circuitry 20 may include a processor 22 and, in some embodiments, such as that illustrated in FIG. 1, may further include memory 24. The processing circuitry may be in communication with or otherwise control a communication interface 26 and, in some embodiments, a user interface (not shown). As such, the processing circuitry may be embodied as a circuit chip (e.g., an integrated circuit chip) configured (e.g., with hardware, software or a combination of hardware and software) to perform operations described herein.

The processor 22 may be embodied in a number of different ways. For example, the processor may be embodied as various processing means such as one or more of a microprocessor or other processing element, a coprocessor, a controller or various other computing or processing devices including integrated circuits such as, for example, an ASIC (application specific integrated circuit), an FPGA (field programmable gate array), or the like. Although illustrated as a single processor, it will be appreciated that the processor may comprise a plurality of processors. The plurality of processors may be in operative communication with each other and may be collectively configured to perform one or more functionalities of the computing device 12 as described herein. The plurality of processors may be embodied on a single computing device or distributed across a plurality of computing devices collectively configured to function as the computing device 12. In some example embodiments, the processor may be configured to execute instructions stored in the memory 24 or otherwise accessible to the processor. As such, whether configured by hardware or by a combination of hardware and software, the processor may represent an entity (e.g., physically embodied in circuitry—in the form of processing circuitry 20) capable of performing operations according to embodiments of the present invention while configured accordingly. Thus, for example, when the processor is embodied as an ASIC, FPGA or the like, the processor may be specifically configured hardware for conducting the operations described herein. Alternatively, as another example, when the processor is embodied as an executor of software instructions, the instructions may specifically configure the processor to perform one or more operations described herein.

In some example embodiments, the memory 24 may include one or more non-transitory memory devices such as, for example, volatile and/or non-volatile memory that may be either fixed or removable. In this regard, the memory may comprise a non-transitory computer-readable storage medium. It will be appreciated that while the memory is illustrated as a single memory, the memory may comprise a plurality of memories. The plurality of memories may be embodied on a single computing device or may be distributed across a plurality of computing devices collectively configured to function as the computing device 12. The memory may be configured to store information, data, applications, instructions and/or the like for enabling the computing device to carry out various functions in accordance with one or more example embodiments. For example, the memory may be configured to buffer input data for processing by the processor 22. Additionally or alternatively, the memory may be configured to store instructions for execution by the processor. As yet another alternative, the memory may include one or more databases that may store a variety of files, contents or data sets, such as the persons database 16 and the plurality of healthcare facility databases 18. Among the contents of the memory, applications may be stored for execution by the processor in order to carry out the functionality associated with each respective application. In some cases, the memory may be in communication with one or more of the processor, user interface, or communication interface 26 via a bus or buses for passing information among components of the computing device.

The user interface may be in communication with the processing circuitry 20 to receive an indication of a user input at the user interface and/or to provide an audible, visual, mechanical or other output to the user. As such, the user interface may include, for example, a keyboard, a mouse, a joystick, a display, a touch screen display, a microphone, a speaker, a Light Emitting Diode (LED), a lighting device, an electronic sensor for capturing human body movements, and/or other input/output mechanisms. In embodiments in which the computing device 12 is implemented on a server, aspects of the user interface may be limited, or the user interface may even be eliminated. For example, the computing device may act as a server or host device, with a user interface provided by a client application.

The communication interface 26 may include one or more interface mechanisms for enabling communication with other devices and/or networks, such as with the healthcare facilities. In this regard, communication with the healthcare facilities includes communication with one or more computing devices of the respective healthcare facilities. In some cases, the communication interface may be any means such as a device or circuitry embodied in either hardware, or a combination of hardware and software that is configured to receive and/or transmit data from/to a network and/or any other device or module in communication with the processing circuitry 20. By way of example, the communication interface may be configured to enable the computing device 12 to communicate with the healthcare facilities 10 via a wireless network, such as a wireless local area network (WLAN), cellular network, and/or the like. Additionally or alternatively, the communication interface may be configured to enable the computing device to communicate with the healthcare facilities via a wireline network. In some example embodiments, the communication interface may be configured to enable communication between the computing device and one or more healthcare facilities via the internet. Accordingly, the communication interface may, for example, include an antenna (or multiple antennas) and supporting hardware and/or software for enabling communications with a wireless communication network (e.g., a wireless local area network, cellular network, and/or the like) and/or a communication modem or other hardware/software for supporting communication via cable, digital subscriber line (DSL), universal serial bus (USB), Ethernet or other methods.

Having now described computing device 12 configured to implement and/or support implementation of various example embodiments, features of several example embodiments will now be described. It will be appreciated that the following features are non-limiting examples of features provided by some example embodiments. Further, it will be appreciated that embodiments are contemplated within the scope of disclosure that implement various subsets or combinations of the features further described herein. Accordingly, it will be appreciated that some example embodiments may omit one or more of the following features and/or implement variations of one or more of the following features.

Referring now to block 30 of FIG. 3, the computing device 12 may include means, such as the processing circuitry 20, the processor 22 or the like, for identifying one or more links between a patient record associated with a person and one or more pre-existing patient records. The person may be a person seeking admittance at a health care facility and, as such, the patient record associated with the person may be created by the respective healthcare facility as part of the admittance procedure. In this regard, the healthcare facility may gather demographic attributes associated with the person and may store those demographic attributes in the patient record. Additionally, the pre-existing patient records may each be created and maintained by the various healthcare facilities 10 and may include, for example, demographic information associated with the corresponding patient, information regarding the encounters of the patient at the healthcare facility including information regarding the clinical context of an encounter, such as the date of the encounter, location of the encounter, the diagnosis, the healthcare provider or the like and documents included in or otherwise associated with a patient record.

In regards to the identification of the one or more links, the computing device 12, such as the processing circuitry 20, may be configured to identify one or more links based upon an analysis of demographic attributes of the person and the respective patients associated with the pre-existing patient records. This analysis of the demographic attributes may be performed in a variety of manners. For example, the computing device, such as the processing circuitry, may be configured to compare the demographic attributes of the person with the corresponding demographic attributes of the respective patients associated with the pre-existing patient records and to identify those pre-existing patient records that are associated with respective patients having demographic attributes that match, either exactly or to at least to within a predetermined threshold, the demographic attributes of the person. However, the computing device, such as the processing circuitry, may be configured to analyze the demographic attributes of the person and the respective patients associated with the pre-existing patient records in other manners and, as such, may identify links between the patient records in any one of a number of different manners.

In one embodiment, the computing device 12 may include means, such as the processing circuitry 20, the processor 22 or the like, for defining, at least temporarily, an initial level of assurance in the respective one or more links that have been identified. See block 32 of FIG. 3. The initial level of assurance may be a probabilistic linking based upon a determination that the demographic attributes of the person and a patient associated with a pre-existing patient record match, either exactly or at least to within a predetermined threshold. Thereafter, the computing device, such as the processing circuitry, may be configured to re-define this initial level of assurance in the respective one or more links based upon external information, as described below.

In this regard and in response to the identification of the one or more links, the computing device 12 may include means, such as the processing circuitry 20, the processor 22, the communications interface 26 or the like, for receiving external information regarding a relationship between the person and the respective patient associated with the pre-existing patient record or regarding confirmation of an identity of the person. See block 34 of FIG. 3. In some instances, the external information is provided by the person seeking admittance to a healthcare facility. As a result of the privacy associated with the visit by a person to a healthcare facility, the healthcare setting may facilitate the provision of external information by the person in order to better define the level of assurance in the links, as described below.

With respect to the relationship between the person and the respective patients associated with the pre-existing patient records, the external information may be the confirmation or denial from the person as to whether the person is the respective patient associated with a pre-existing patient record. In this regard, the computing device 12, such as the processing circuitry 20, the communications interface 26 or the like, may be configured to provide information regarding each pre-existing patient record that has been identified to the healthcare facility at which the person is seeking admittance. In particular, the computing device, such as the processing circuitry, may be configured to provide information regarding the pre-existing patient records that have been identified to be linked to the patient record associated with the person to a computing device of the healthcare facility. The computing device of the healthcare facility may prompt a healthcare practitioner to inquire of the person as to whether the person is the respective patient associated with each of the pre-existing patient records that have been identified.

In order to permit the person to identify the pre-existing patient record, information regarding the pre-existing patient record may be provided to the person, such as the clinical context of the patient record, e.g., the date of an encounter, the location of an encounter, the diagnosis, the provider, etc. In response, the person may indicate whether they were the patient associated with a respective pre-existing patient record. This confirmation or denial as to whether the person is the respective patient associated with the pre-existing patient record may be received by the computing device 12 as external information regarding the relationship between the person and the respective patients associated with the pre-existing patient record.

With respect to the confirmation of an identity of the person, the external information may be an identification credential provided by the person to the healthcare facility to which the person is seeking admittance or biometric information, such as a fingerprint scan, a retinal scan, a DNA sample or the like, that is provided by the person to the healthcare facility to which the person is seeking admittance. As such, the computing device 12, such as the processing circuitry 20, the communications interface 26 or the like, may be configured to receive confirmation of the identity of the person based upon an identification credential, such as a driver's license, a military identification card, a passport or the like, or based upon biometric information.

As shown in block 36 of FIG. 3, the computing device 12 may also include means, such as the processing circuitry 20, the processor 22 or the like, for defining a level of assurance in the respective one or more links based upon the external information. In this regard, the computing device, such as the processing circuitry, may be configured to define a level of assurance for each link that has been identified based upon the external information. In an embodiment in which an initial level of assurance was defined in one or more links that have been identified, the initial level of assurance in the respective one or more links may be re-defined based upon the external information. By way of an example as will be described hereinafter, a lower level of assurance may be defined in an instance in which the person denies that the person is a respective patient associated with a pre-existing record, while a higher level of assurance in the link to a pre-existing record may be defined in an instance in which the person confirms that the person is the respective patient associated with a pre-existing record. Additionally, the computing device, such as a processing circuitry, may define a greater level of assurance in a link to a pre-defined record in an instance in which the person provides an acceptable identification credential and an even greater level of assurance in a link to a pre-existing record in an instance in which the person provides biometric information that positively identifies the person.

Figure 4:
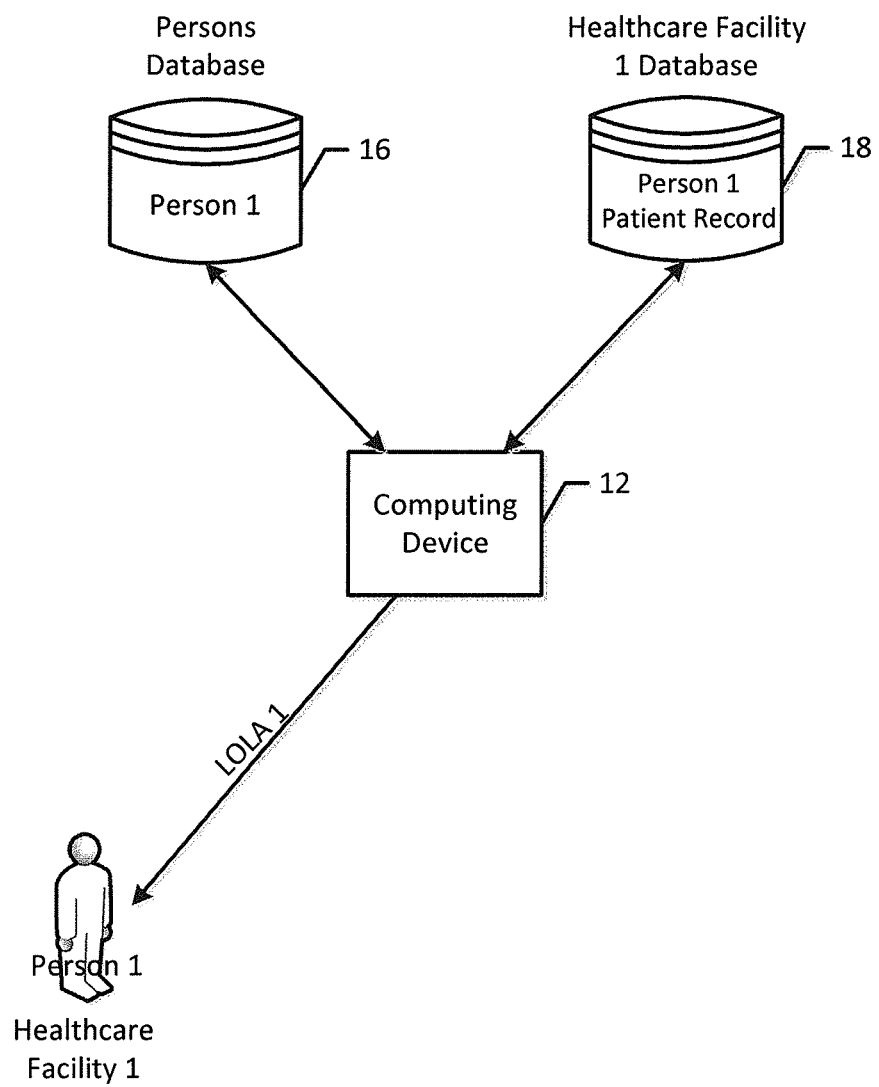
Figure 5:
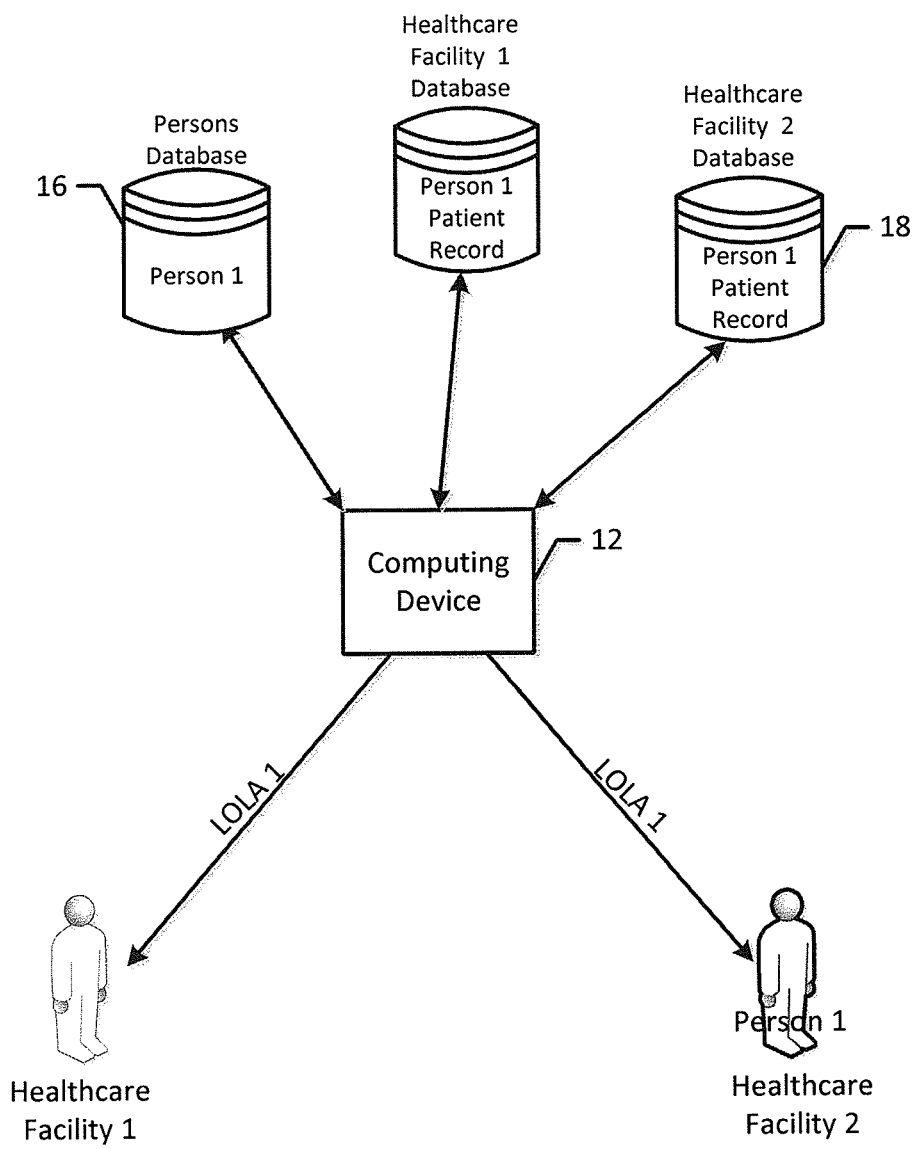

In the example depicted in FIG. 4, a person, designated Person 1, may arrive at the Healthcare Facility 1. In an instance in which Person 1 is a new patient for Healthcare Facility 1 and in conjunction with the admittance process, Person 1 may provide Healthcare Facility 1 with demographic information associated with Person 1, such as first name, last name, date of birth, residential address including zip code, etc. Healthcare Facility 1 may, in turn, provide the demographic information associated with Person 1 to the computing device 12 and the computing device may compare the demographic information associated with Person 1 to the demographic information associated with the various patients that have been previously identified by the computing device. As shown in the embodiment of FIG. 4, the computing device may include or otherwise be associated with a persons database 16 and a plurality of healthcare facility databases 18, one of which is associated with each respective healthcare facility that provides patient records to the computing device. The healthcare facility databases may store the patient records provided by the respective healthcare facilities. As the patient records provided by the healthcare facilities to the computing device are generally only a portion of the entire patient record maintained by the healthcare facility, such as the demographic attributes of the patient as well as information relating to the clinical context, such as a date of encounter, location of encounter, a diagnosis and/or provider, the patient records stored by the healthcare facility databases may likewise be a portion of the entire patient records maintained by the healthcare facilities. The persons database may store a unique patient identifier for each patient that has been identified by the computing device, such as a result of patient records having been provided. The persons database may also store links or pointers to the patient records for a respective patient that are stored by the healthcare facility databases.

In an instance in which the computing device 12, such as the processing circuitry 20, does not identify Person 1 as a patient that had been previously identified by the computing device, the computing device, such as the processing circuitry, the memory 24 or the like, may be configured to create a record for Person 1 in the persons database 16 as well as a patient record for Person 1 that includes the demographic attributes associated with Person 1 in the Healthcare Facility 1 database. Additionally, the computing device, such as the processing circuitry, may be configured to identify a link between the record associated with Person 1 that has now been created by the computing device in the persons database and the patient record associated with Person 1 that is to be created by Healthcare Facility 1 upon the admittance of Person 1. In FIG. 4, the link that is created is illustrated by the directional line extending from the computing device to Healthcare Facility 1.

In the illustrated embodiment, the computing device 12, such as the processing circuitry 20, may be configured to define, at least temporarily, the initial level of assurance in the link between the record associated with Person 1 that has been created by the computing device and stored in the persons database 16 and the patient record that is to be created by Healthcare Facility 1 upon admittance of Person 1. In the illustrated embodiment, the initial level of assurance is identified as a level of link assurance (LOLA) 1. While numeric designations of LOLA 0, LOLA 1, LOLA 2, LOLA 3 and LOLA 4 will be referenced in conjunction with the following example, any number of levels of assurance may be defined and these levels of assurance may be identified in any of a variety of different manners in other embodiments.

In an instance in which Person 1 does not provide confirmation of their identity, such as an identification credential or biometric information, the level of assurance in the respective link between the patient record for Person 1 maintained by the computing device and the patient record to be created for Person 1 upon admittance to Healthcare Facility 1 may remain at the initial level of assurance, such as LOLA 1. Thereafter, in an instance in which the same person, that is, Person 1, visits a second healthcare facility, such as Healthcare Facility 2, Healthcare Facility 2 may receive demographic attributes associated with Person 1 during the admittance process and may provide those demographic attributes to the computing device 12. Upon comparing the demographic attributes associated with Person 1 that were provided by Healthcare Facility 2 with demographic attributes associated with the various patients that have been previously identified by the computing device, such as by a review of demographic attributes stored in the patient records in the healthcare facility databases (which may be directed by the links to the various patient records that are stored by the persons database in association with each unique patient identifier), the computing device, such as the processing circuitry, may identify Person 1 to potentially be the same person as the patient that previously visited Healthcare Facility 1. As such, the computing device, such as a processing circuitry, may define a patient record for Person 1 in the Healthcare Facility 2 database with the patient record including the demographic attributes of Person 1 provided by Healthcare Facility 2. Additionally, the computing device, such as the processing circuitry, may initially define a link between the patient record defined by the computing device and stored, for example, in the Healthcare Facility 2 database and the patient record to be created by Healthcare Facility 2 upon admission of the Person 1. See, for example, FIG. 5 in which an initial link between the computing device and Healthcare Facility 2 is identified as a LOLA 1 link.

Figure 6:
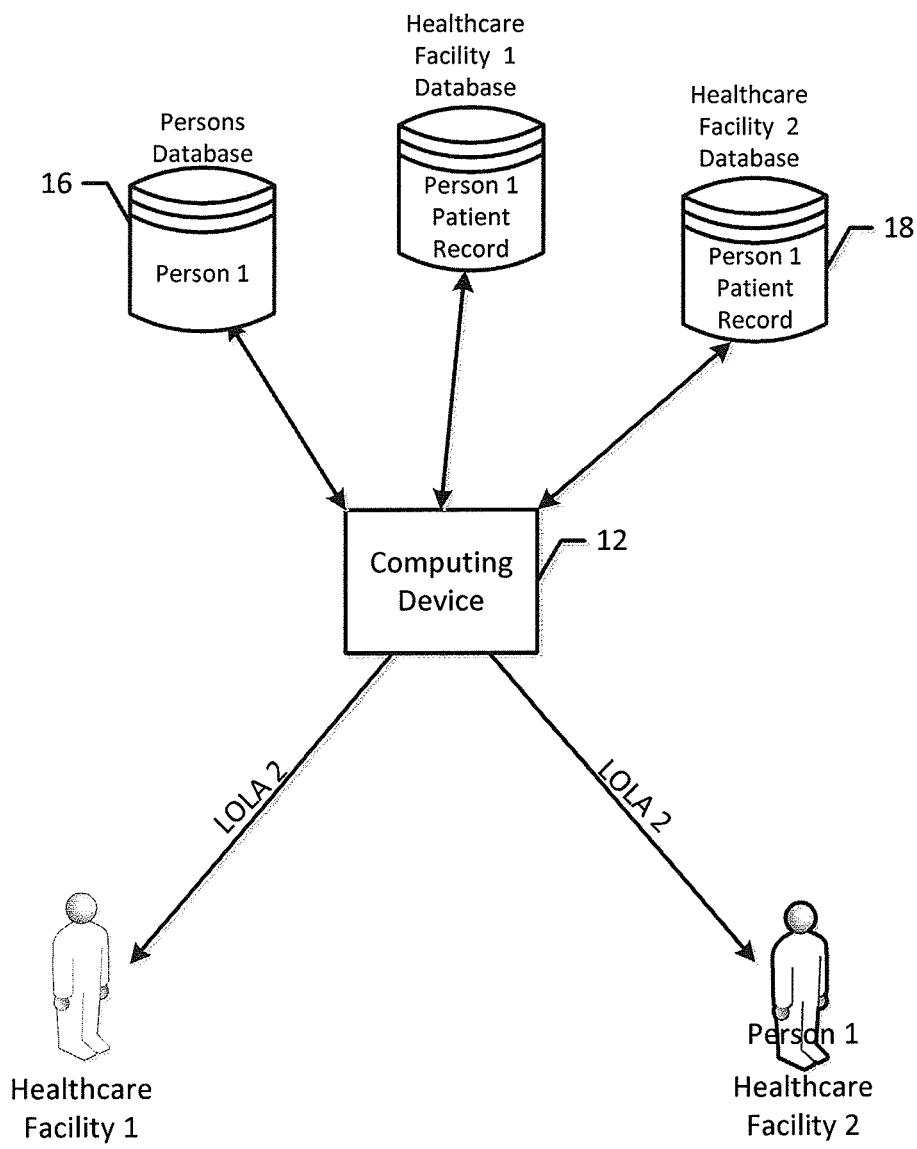

In addition to identifying Person 1 as potentially being the same person as the patient that previously visited Healthcare Facility 1, the computing device 12, such as the processing circuitry 20, the processor 22, the memory 24 or the like, may be configured to identify the patient record for Person 1 that is stored by Healthcare Facility 1 to be associated with a patient who may potentially match Person 1. As such, the computing device, such as the processing circuitry, may prompt Healthcare Facility 2 to inquire of Person 1 as to whether the patient record created by Healthcare Facility 1 was a product of Person 1's prior visit to Healthcare Facility 1 or whether the patient record maintained by Healthcare Facility 1 is for a different patient. In this regard, the computing device, such as the processing circuitry, the communications interface 26 or the like, may be configured to provide information regarding the patient record created by Healthcare Facility 1 and stored, for example, by the Healthcare Facility 1 database, such as providing information regarding the demographic attributes and the clinical context, such as the date of encounter, location of encounter, diagnosis and provider, associated with the patient that visited Healthcare Facility 1 to Healthcare Facility 2 in order to prompt the recollection of Person 1 of the visit to Healthcare Facility 1. In an instance in which Person 1 confirms that the patient record created by Healthcare Facility 1 relates to their prior visit to Healthcare Facility 1, the computing device, such as the processing circuitry, may be configured to re-define the level of assurance associated with the links between the patient record associated with Person 1 and maintained by the computing device, such as the persons database 16, and the patient records created by Healthcare Facilities 1 and 2 for Person 1. As shown in FIG. 6, for example, the computing device, such as the processing circuitry, may re-define the level of assurance of these links to be LOLA 2, thereby having a greater level of assurance than the initial level of assurance of LOLA 1. Although the initial level of assurance, e.g., LOLA 1, may be defined based upon the probabilistic linking of patient records as a result of a comparison of the respective demographic attributes, the greater levels of assurance, e.g., LOLA 2, LOLA 3, LOLA 4, etc., are based upon external information and may be established through a common patient record, such as maintained by the persons database. Although this example only includes a single pre-existing patient record, the computing device, such as the processing circuitry, may identify a plurality of pre-existing patient records created and maintained by one or more other healthcare facilities and the computing device may cause Healthcare Facility 2 to separately inquire of Person 1 as to whether each of these patient records relates to Person 1, or not.

Additionally, in an instance in which Person 1 denies that a pre-existing patient record that has been identified as a potential match is a product of their prior visit to another healthcare facility, the computing device 12, such as the processing circuitry 20, may be configured to re-define the level of assurance in the link between the patient record maintained by the computing device and the patient record maintained by the other healthcare facility, such as from a LOLA 1 to a LOLA 0, thereby indicating a lower level of assurance in the respective link, such as may be representative of having no confidence in the respective link being associated with Person 1.

Figure 7:
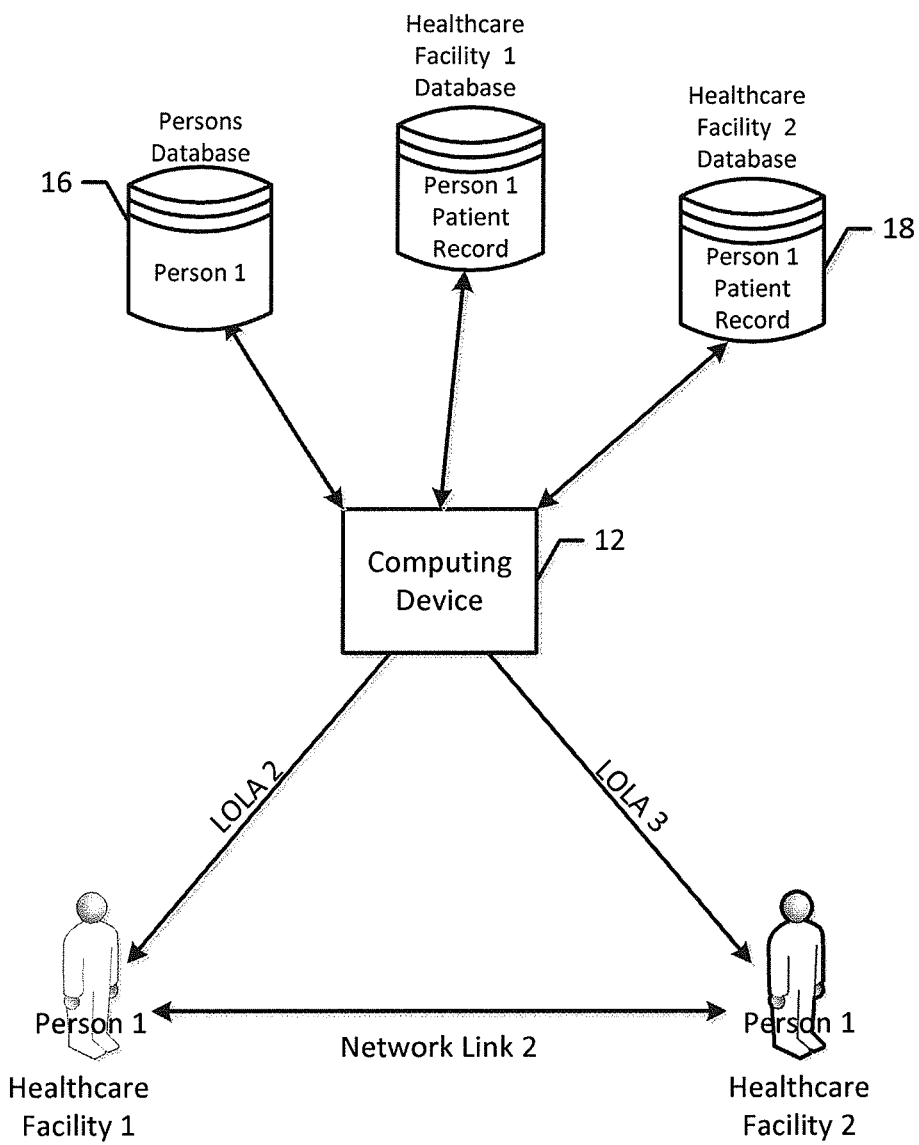

In addition to confirming that Person 1 is the respective patient associated with the pre-existing patient record created by Healthcare Facility 1, Person 1 may provide confirmation of their identity to Healthcare Facility 2, such as in the form of an identification credential, e.g., a driver's license. In response to the confirmation of the identity of Person 1 with an identification credential, the computing device 12, such as the processing circuitry 20, may again re-define the level of assurance in the link between the patient record for Person 1 maintained by the computing device and the patient record for Person 1 to be created by Healthcare Facility 2. In one embodiment, the computing device, such as the processing circuitry, is configured to re-define the level of assurance in the respective link by increasing the level of assurance in the respective link, such as to LOLA 3 as shown in FIG. 7 so as to indicate an even greater level of assurance in the link. If Person 1 had been identified as a result of biometric information, instead of an identification credential, the computing device, such as the processing circuitry, may have further re-defined the level of assurance in the respective link, such as by further increasing the level of assurance in the respective link, such as to LOLA 4.

Once links have been identified between a patient record associated with a person, such as the patient record created by Healthcare Facility 2 for Person 1, and pre-existing patient records, such as the patient record for Person 1 previously created by Healthcare Facility 1, the computing device 12, such as the processing circuitry 20, may establish a network link directly between the healthcare facilities such that at least portions of the patient records may be shared. In this regard, portions of the patient record for Person 1 created by Healthcare Facility 1 may be shared with Healthcare Facility 2 in order to provide a more complete picture of Person 1's healthcare history. In this example embodiment, the additional information stored within the patient record for Person 1 that was created by Healthcare Facility 1 and that has not been previously shared with the computing device may be shared directly with Healthcare Facility 2, but not with the computing device so as to limit the distribution of the information.

As shown in block 40 of FIG. 3, the computing device 12 may include means, such as the processing circuitry 20 or the like, for permitting different actions to be taken with respect to the pre-existing patient records depending upon the level of assurance in the links between the patient records. Various actions may be permitted depending upon the level of assurance of the network link, such as the provision of access to information regarding prior encounters of the patient as documented by the pre-existing patient record, the provision of access to documentation associated with the pre-existing patient record or the like.

As shown in the example of FIG. 7, a network link may be established between Healthcare Facilities 1 and 2 to facilitate the sharing of information regarding the pre-existing patient record created by Healthcare Facility 1 with Healthcare Facility 2. In the illustrated embodiment, the computing device 12, such as the processing circuitry 20, defines the level of assurance in the network link established between the healthcare facilities to be the lowest level of assurance of those links that have been identified between the healthcare facilities and the patient records for Person 1 maintained by the computing device, such as a level of assurance 2 in the illustrated embodiment. Based upon the level of assurance of the network link, the computing device, such as the processing circuitry, may permit different actions to be taken with respect to the pre-existing patient record, such as by sharing information regarding the prior encounters of Person 1 at Healthcare Facility 1, but not sharing the documentation associated with the patient record created by Healthcare Facility 1. In an instance in which each of the links between the patient records for Person 1 maintained by the healthcare facilities and the patient records for Person 1 maintained by the computing device have a greater level of assurance, the network link established between the healthcare facilities would also have a greater level of assurance such that documentation associated with the pre-existing patient records may also be shared.

Figure 8:
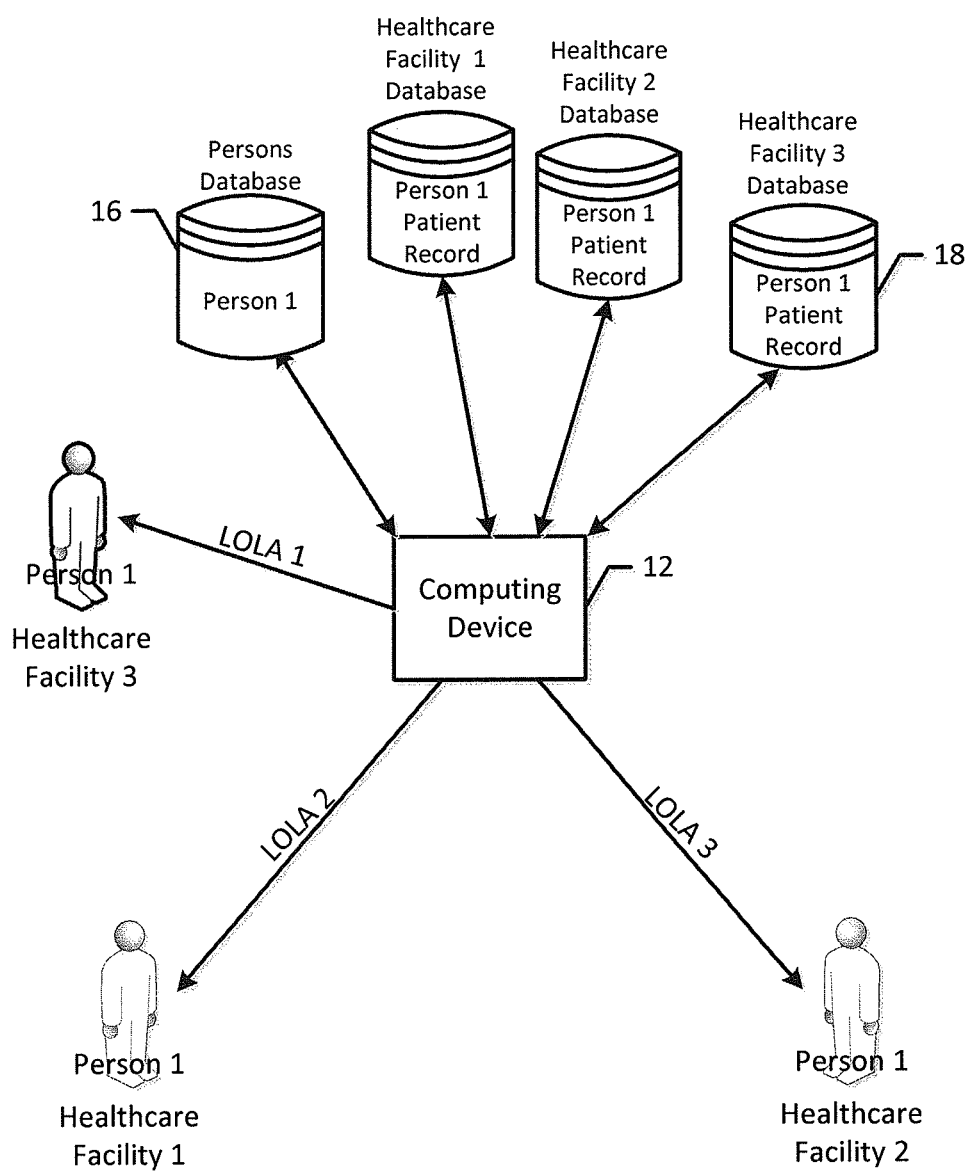

Continuing with the foregoing example, FIG. 8 illustrates a situation in which Person 1 has now visited Healthcare Facility 3. In response to the receipt of demographic attributes associated with Person 1 from Healthcare Facility 3, the computing device 12, such as the processing circuitry 20, may define and store a patient record associated with Person 1 in a database for Healthcare Facility 3, such as in memory 24. Additionally, the computing device may establish a link between the patient record for Person 1 that has been created by the computing device and the patient record for Person 1 that is to be created by Healthcare Facility 3. The computing device may also define an initial level of assurance, such as LOLA 1, for the newly established link. The computing device, such as a processing circuitry, may also identify other patient records potentially related to Person 1 based upon a review of the patient records stored in the various healthcare facility databases 18 maintained by the computing device. In this regard, the computing device, such as the processing circuitry, may identify pre-existing patient records that have been created by Healthcare Facilities 1 and 2.

Figure 9:
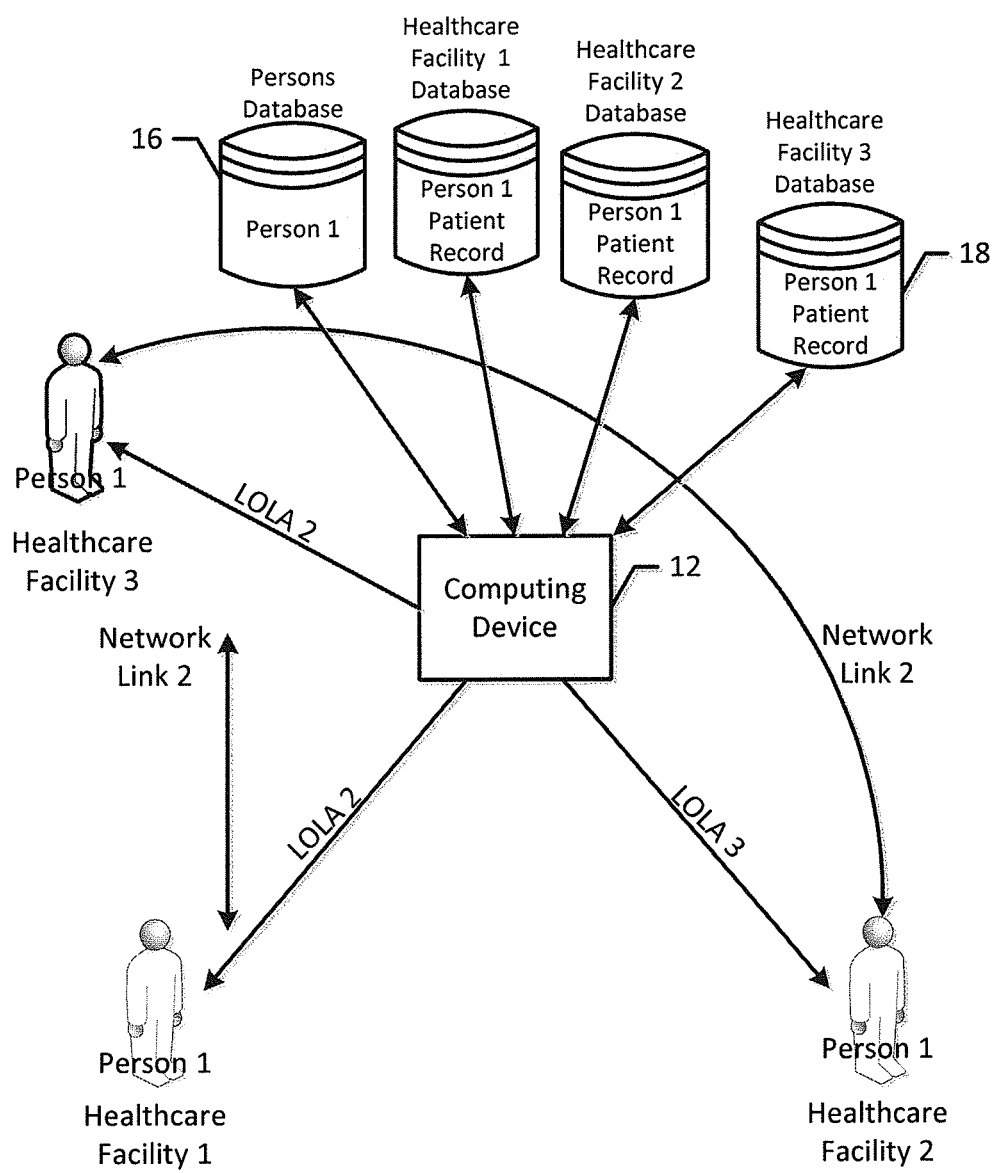

The computing device 12, such as the processing circuitry 20, may prompt Healthcare Facility 3 to inquire of Person 1 as to whether the pre-existing patient records relate to his/her prior visits to Healthcare Facilities 1 and 2, or not. In an instance in which Person 1 confirms that the pre-existing patient records that have been identified by the computing device relate to his/her prior visits to Healthcare Facilities 1 and 2, the level of assurance of the link that has been created between the patient record of the computing device and the patient record to be created by Healthcare Facility 3 may be re-defined, such as by being increased to LOLA 2 as shown in FIG. 9. Additionally, the computing device, such as the processing circuitry, may establish network links between Healthcare Facility 3 and Healthcare Facilities 1 and 2 in order to provide access by Healthcare Facility 3 to the pre-existing patient records for Person 1 that have been created and stored by Healthcare Facilities 1 and 2. As described above, the level of assurance of each network link may be defined to be the lower level of assurance of the links between the respective healthcare facilities and the computing device in conjunction with the patient records for Person 1.

Figure 10:
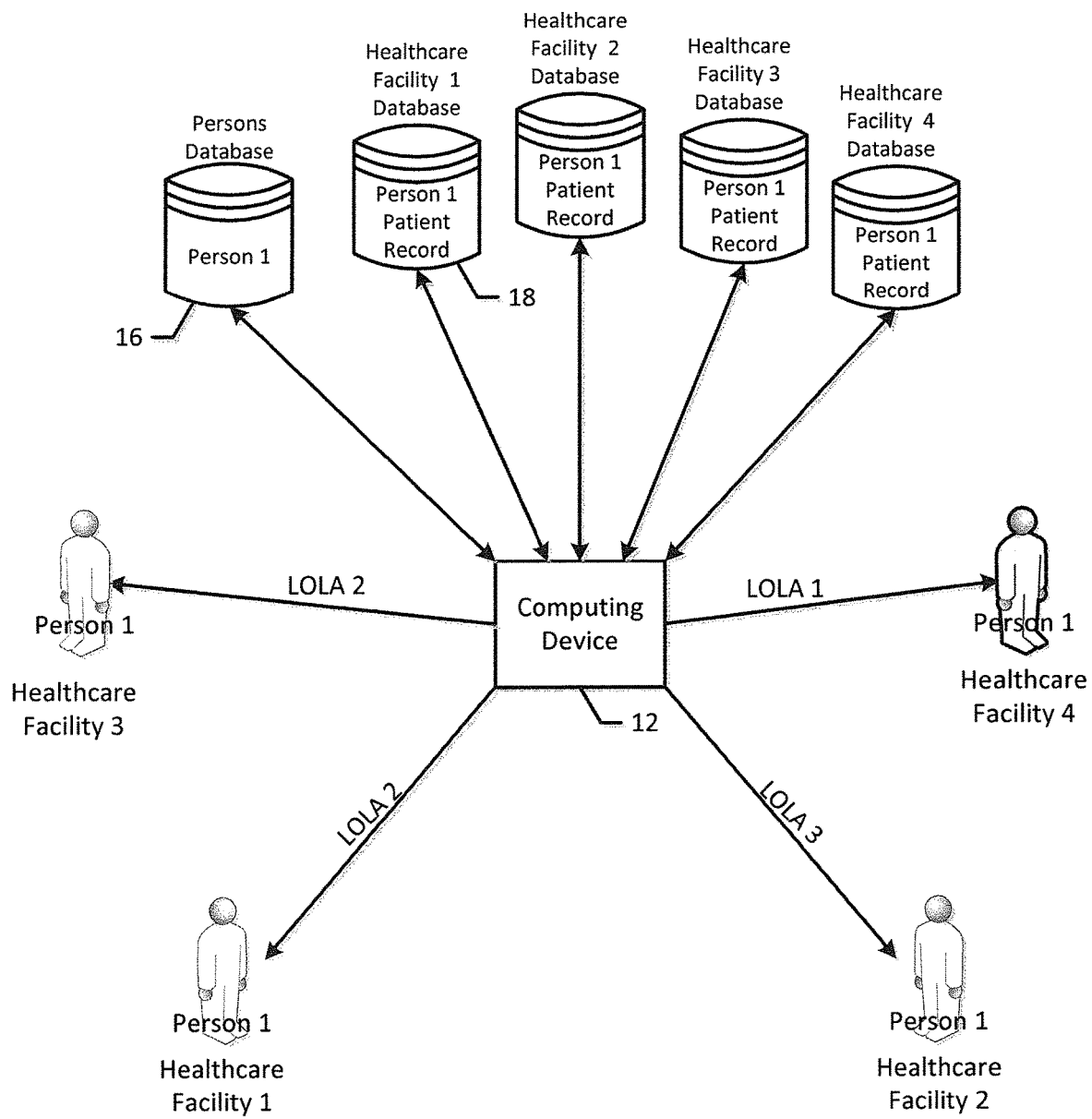

Further, if Person 1 subsequently visits Healthcare Facility 4, the computing device 12, such as the processing circuitry 20, may be configured to establish a patient record for Person 1 in the database associated with Healthcare Facility 4 based upon the demographic attributes provided by Healthcare Facility 4 to the computing device for Person 1. Additionally, the computing device, such as the processing circuitry, may identify a link between the patient record for Person 1 created by the computing device and the patient record to be created by Healthcare Facility 4 for Person 1 and may define an initial level of assurance in the link, such as LOLA 1 as shown in FIG. 10. In an instance in which the computing device, such as the processing circuitry, receives external information from Healthcare Facility 4 regarding the confirmation of the identity of Person 1 in the form of biometric information, the computing device, such as the processing circuitry, may re-define the level of assurance in the link between the patient record for Person 1 created by the computing device and the patient record for Person 1 to be created by Healthcare Facility 4, such as by increasing the level of assurance, such as to LOLA 4 as shown in FIG. 11.

Figure 11:
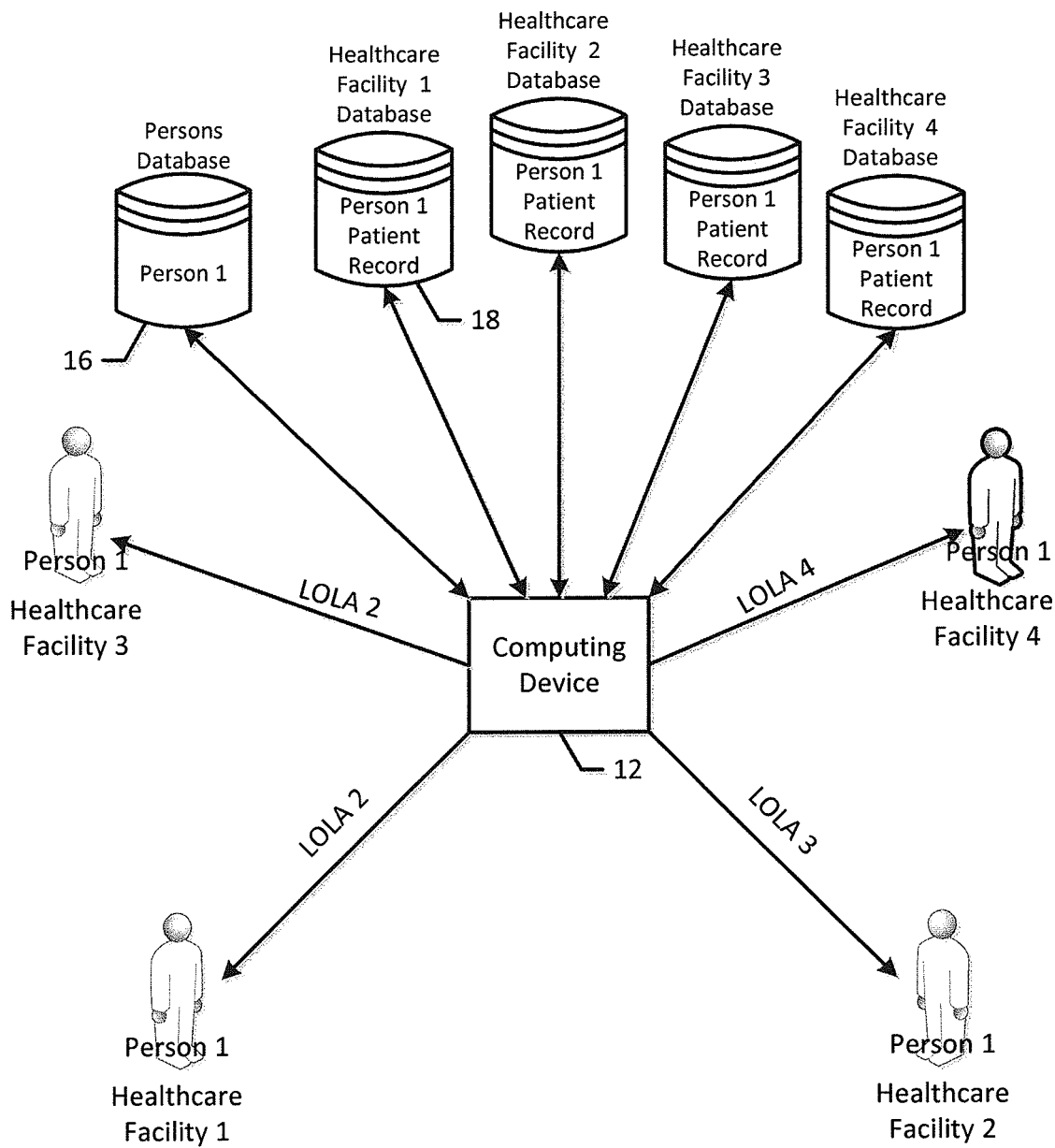

Although not shown in FIG. 11, the computing device 12, such as the processing circuitry 20, of this example embodiment may also be configured to identify the pre-existing patient records of Healthcare Facilities 1, 2 and 3 that may be associated with the same person and may cause Healthcare Facility 4 to inquire of Person 1 as to whether the pre-existing patient records identified at Healthcare Facilities 1, 2 and 3 relate to their prior visits to Healthcare Facilities 1, 2 and 3, or not. Thereafter, the computing device, such as the processing circuitry, may establish network links between Healthcare Facilities 1, 2 and/or 3 and Healthcare Facility 4 in order to share information regarding the pre-existing patient records for Person 1 that have been created and stored by Healthcare Facilities 1, 2 and/or 3 with Healthcare Facility 4 in order to provide a healthcare practitioner at Healthcare Facility 4 with a more complete history of the patient's prior healthcare.

As illustrated by the foregoing example, the links between a patient record associated with a person and pre-existing patient records that are identified by the computing device 12, such as the processing circuitry 20, would not only include the links that extend directly between the respective patient records, such as the network links, but also the links between a pre-existing patient record created and stored by a healthcare facility and a patient record created and maintained by the computing device in association with the same person.

Following the definition of the level of assurance in one or more links based upon external information, the computing device 12, such as the processing circuitry 20, the communications interface 26 or the like, may be configured to receive additional external information and, as a result, may re-define the level of assurance in the respective link. As shown in block 38 of FIG. 3, for example, the computing device, such as the processing circuitry, the communications interface or the like, may be configured to determine if further external information has been received and, if so, to permit the level of assurance to be re-defined in a respective link. By way of example, Person 1 could return to Healthcare Facility 1 following his/her visit to Healthcare Facility 4. Upon his/her return to Healthcare Facility 1, Person 1 could provide additional external information in the form of biometric information, such as a fingerprint scan, that confirms the identity of Person 1. In this example, the computing device, such as the processing circuitry, may be configured to re-define the level of assurance in the link between the patient record for Person 1 created by Healthcare Facility 1 and the patient record for Person 1 created by the computing device, such as to LOLA 4.

Examples of external information that may be utilized in order to define the level of assurance have been provided. However, other types of external information may be utilized in other embodiments. For example, the computing device 12, such as the processing circuitry 20, the communication interface 26 or the like, may be configured to receive external information from a third party verification service, such as a credit checking service, an address verification service, an identity assurance service or the like. Based upon the external information received from the third party verification service in this embodiment, the computing device, such as the processing circuitry, may be configured to define the level of assurance based at least in part thereupon. For example, a greater level of assurance may be provided in an instance in which an address verification service confirms the address of the patient that was provided by the patient and a lower level of assurance being defined in an instance in which an address verification service fails to confirm the address provided by the patient.

In one embodiment, the external information regarding the confirmation of the identity of the person may have an associated authority, such as an associated strength. For example, certain forms of identification credentials may have a greater reliability as a result of, for example, increased efforts to confirm the identity of the person prior to the issuance of the identification credential such that the resulting identification credential has more authority than other identification credentials that were issued with less stringent confirmation measures. In this embodiment, the computing device 12, such as the processing circuitry 20, may be configured to define the level of assurance in the links based at least in part upon the authority of the external information regarding confirmation of the identity of the person. As such, links associated with a person whose identity is confirmed with an identification credential having a greater authority may have a greater level of assurance than links associated with a person having an identity confirmed with an identification credential having a lesser degree of authority.

While a variety of types of external information that may be utilized in order to define the level of assurance in respective links between patient records has been described and may be utilized by a computing device 12, additional forms of external information that may be utilized to define the level of assurance in respective links may be identified in the future. As such, the computing device, such as the processing circuitry 20, may be configured to permit the external information that is received and that is utilized in order to define the level of assurance in respective links between patient records to be extended, such as by permitting additional or different types of external information to be received and utilized in order to define the level of assurance in links between patient records. In one example embodiment, the computing device, such as the processing circuitry, may have a plug-in architecture in order to permit extension of the external information that may be received and relied upon in the definition of the level of assurance in the respective links between patient records.

In addition to the external information, the computing device 12, such as the processing circuitry 20, of one example embodiment may be configured to define the level of assurance based upon one or more additional factors. For example, the computing device, such as the processing circuitry, may be configured to define the level of assurance based upon the number of patient care settings that have received equivalent external information regarding the relationship between the person and the respective patients associated with the pre-existing patient records or regarding confirmation of the identity of the person. For example, in an instance in which links are identified between patient records at two different healthcare facilities and the two different healthcare facilities have each received equivalent external information, such as a driver's license of the patient or biometric information of the patient, the computing device, such as the processing circuitry, may be configured to further increase the level of assurance in the respective links relative to an instance in which the healthcare facilities had received different types of external information.

As another example, the computing device 12, such as the processing circuitry 20, may be configured to define the level of assurance in the respective one or more links based at least in part upon a level of assurance associated with the healthcare facility that receives the external information from the person. For example, some healthcare facilities may be more reliable than the other healthcare facilities in regards to creating valid patient records with a minimal percentage of duplicate patient records. As a result, the level of assurance in the links that are established with the patient records created by a more reliable healthcare facility may be greater than the level of assurance in the links created by a healthcare facility that is less reliable, such as a healthcare facility that creates a greater percentage of duplicate patient records.

In regards to the definition of the level of assurance in one or more links, the computing device 12, such as the processing circuitry 20, of one embodiment may re-define the initial level of assurance in an instance in which the external information is provided in association with both the patient record associated with the person and the pre-existing patient record linked thereto. In this regard, the computing device, such as the processing circuitry, may define the links to have a greater level of assurance in an instance in which external information is provided bilaterally in association with both patient records, as opposed to the external information being provided only in conjunction with one of the patient records.

By permitting the level of assurance to be defined, at least in part, upon external information, the resulting levels of assurance in the links between patient records may be defined with more precision. Thus, actions that may be taken based upon the level of assurance in the respective links may be similarly controlled in a more defined and reliable fashion. Additionally, healthcare practitioners may have a more reliable indicator of the likelihood of a pre-existing patient record that has been identified as a match actually being related to the same person, thereby increasing the confidence that the healthcare practitioner may have in relying upon or otherwise referencing the pre-existing patient records.

As described above, FIG. 3 illustrates a flowchart of a system, method, and computer program product according to example embodiments of the invention. It will be understood that each block of the flowchart, and combinations of blocks in the flowchart, may be implemented by various means, such as hardware and/or a computer program product comprising one or more computer-readable mediums having computer readable program instructions stored thereon. For example, one or more of the procedures described herein may be embodied by computer program instructions of a computer program product. In this regard, the computer program product(s) which embody the procedures described herein may be stored by one or more memory devices 24 of a computing device 12 and executed by processing circuitry 20 in the computing device. In some embodiments, the computer program instructions comprising the computer program product(s) which embody the procedures described above may be stored by memory devices of a plurality of computing devices. As will be appreciated, any such computer program product may be loaded onto a computer or other programmable apparatus to produce a machine, such that the computer program product including the instructions which execute on the computer or other programmable apparatus creates means for implementing the functions specified in the flowchart block(s). Further, the computer program product may comprise one or more computer-readable memories on which the computer program instructions may be stored such that the one or more computer-readable memories can direct a computer or other programmable apparatus to function in a particular manner, such that the computer program product comprises an article of manufacture which implements the function specified in the flowchart block(s). The computer program instructions of one or more computer program products may also be loaded onto a computer or other programmable apparatus to cause a series of operations to be performed on the computer or other programmable apparatus to produce a computer-implemented process such that the instructions which execute on the computer or other programmable apparatus implement the functions specified in the flowchart block(s).

Accordingly, blocks or steps of the flowchart support combinations of means for performing the specified functions and combinations of steps for performing the specified functions. It will also be understood that one or more blocks of the flowchart, and combinations of blocks in the flowchart, may be implemented by special purpose hardware-based computer systems which perform the specified functions or steps, or combinations of special purpose hardware and computer program product(s).

The above described functions may be carried out in many ways. For example, any suitable means for carrying out each of the functions described above may be employed to carry out embodiments of the invention. In one embodiment, a suitably configured processing circuitry 20 may provide all or a portion of the elements of the invention. In another embodiment, all or a portion of the elements of the invention may be configured by and operate under control of a computer program product. The computer program product for performing the methods of embodiments of the invention includes a computer-readable storage medium, such as the non-volatile storage medium, and computer-readable program code portions, such as a series of computer instructions, embodied in the computer-readable storage medium.

Many modifications and other embodiments of the inventions set forth herein will come to mind to one skilled in the art to which these inventions pertain having the benefit of the teachings presented in the foregoing descriptions and the associated drawings. Therefore, it is to be understood that the embodiments of the invention are not to be limited to the specific embodiments disclosed and that modifications and other embodiments are intended to be included within the scope of the appended claims. Moreover, although the foregoing descriptions and the associated drawings describe example embodiments in the context of certain example combinations of elements and/or functions, it should be appreciated that different combinations of elements and/or functions may be provided by alternative embodiments without departing from the scope of the appended claims. In this regard, for example, different combinations of elements and/or functions than those explicitly described above are also contemplated as may be set forth in some of the appended claims. Although specific terms are employed herein, they are used in a generic and descriptive sense only and not for purposes of limitation.

The invention claimed is:

1. A method implemented within a health information infrastructure, comprising at least a computer device, the method comprising:
  identifying, with processing circuitry of the computer device functioning within the health information infrastructure, one or more links between a patient record associated with a person who has visited a first healthcare facility and pre-existing patient records from at least a second healthcare facility, wherein each pre-existing patient record has a plurality of demographic attributes associated with a patient, and wherein identifying one or more links comprises identifying one or more links based upon an analysis of demographic attributes of the person and the respective patients associated with the pre-existing patient records;
  defining an initial level of assurance in the respective one or more links in response to identification of the one or more links, the initial level of assurance being based on a probabilistic analysis of the plurality of demographic attributes of the person and the demographic attributes of the patients associated with the pre-existing patient records;
  maintaining a record of each of a plurality of persons in a persons database and storing patient records provided by respective healthcare facilities in one or more healthcare facility databases, wherein the patient records stored in one or more healthcare facility databases comprise at least a portion of corresponding patient records maintained by the respective healthcare facilities, and wherein identifying the one or more links comprises modifying the persons database to include a pointer from the record of the person who has visited the first healthcare facility to one or more of the pre-existing patient records of at least the second healthcare facility for which a link has been identified;
  in response to identification of the one or more links, providing information, via a communications interface of the computer device functioning within the health information infrastructure, to the first healthcare facility visited by the person regarding the pre-existing patient records from at least the second healthcare facility for which a link has been identified with the patient record associated with the person and receiving external information, via the communications interface of the computer device functioning within the health information infrastructure, provided by the person at the first healthcare facility regarding a relationship between the person and the respective patients associated with the pre-existing patient records or regarding confirmation of an identity of the person;
  defining, with the processing circuitry of the computer device functioning within the health information infrastructure, a level of assurance in the respective one or more links based upon the external information;
  causing a network link to be established, by the processing circuitry of the computer device functioning within the health information infrastructure, between the first and second healthcare facilities to permit at least portions of the patient records to be shared based upon the level of link assurance; and
  following establishment of the network link, controlling actions taken based upon the level of assurance in the links to the respective patient records by permitting different actions to be taken with respect to the pre-existing patient records depending upon the level of assurance in the links to the respective patient records, wherein controlling actions taken based upon the level of assurance in the links comprises communicating, responsive to a request by the person for admission at the first health care facility, information from the pre-existing patient records regarding a prior encounter of the person but not documentation associated with the prior encounter from the second health care facility to the first health care facility in an instance in which the link has a first level of assurance and communicating, responsive to the request by the person for admission at the first health care facility, information from the pre-existing patient records regarding the prior encounter of the person as well as documentation associated with the prior encounter from the second health care facility to the first health care facility in an instance in which the link has a second level of assurance;
  wherein defining the level of assurance comprises redefining the initial level of assurance in the respective one or more links based upon the external information.

2. A method according to claim 1 wherein causing a network link to be established between the first and second healthcare facilities comprises causing the network link to be established via an application programming interface (API) or via a portal application.

3. A method according to claim 1 wherein re-defining the initial level of assurance comprises re-defining the initial level of assurance in an instance in which external information is provided in association with both the patient record associated with the person and a pre-existing patient record linked thereto.

4. A method according to claim 1 further comprising re-defining the level of assurance in a respective link in response to receipt of further external information following definition of the level of assurance.

5. A method according to claim 1 wherein receiving external information comprises receiving confirmation or denial from the person as to whether the person is the respective patient associated with a pre-existing patient record.

6. A method according to claim 1 wherein receiving external information comprises receiving confirmation of an identity of the person based upon an identification credential.

7. A method according to claim 1 wherein receiving external information comprises receiving confirmation of an identity of the person based upon biometric information.

8. A method according to claim 1 wherein receiving external information comprises receiving external information from a third party verification service such that the level of assurance is defined based at least in part upon the external information from the third party verification service.

9. A method according to claim 1 wherein the external information regarding confirmation of the identity of the person has an associated authority, and wherein defining the level of assurance in the respective one or more links is based at least in part upon the authority of the external information regarding confirmation of the identity of the person.

10. A method according to claim 1 further comprising permitting the external information that is received and upon which the level of assurance is defined to be extended by permitting additional or different types of external information to be received and utilized in order to define the level of assurance in links between patient records.

11. A method according to claim 1 wherein defining the level of assurance further comprises defining the level of assurance based upon a number of patient care settings that have received external information regarding a relationship between the person and the respective patients associated with the pre-existing patient records or regarding confirmation of the identity of the person.

12. A method according to claim 1 wherein defining the level of assurance further comprises defining the level of assurance in the respective one or more links based at least in part upon a level of assurance associated with a healthcare facility that receives the external information from the person.

13. A method according to claim 1 further comprising permitting different actions to be taken with respect to the pre-existing patient records depending upon the level of assurance in the links to the respective patient records.

14. A health information computing device associated with a health information infrastructure, the health information computing device comprising:

a processing circuitry, comprising at least a processor and memory including computer program code;
a persons database configured to store a record of each of a plurality of persons; and
one or more healthcare facility databases configured to store patient records provided by respective healthcare facilities, wherein the patient records stored in one or more healthcare facility databases comprise at least a portion of corresponding patient records maintained by the respective healthcare facilities, and
wherein the health information computing device associated with the health information infrastructure is configured to:
identify one or more links between a patient record associated with a person who has visited a first healthcare facility and pre-existing patient records from at least a second healthcare facility, wherein each pre-existing patient record has a plurality of demographic attributes associated with a patient, and wherein identifying one or more links comprises identifying one or more links based upon an analysis of demographic attributes of the person and the respective patients associated with the pre-existing patient records, wherein identifying the one or more links comprises modifying the persons database to include a pointer from the record of the person who has visited the first healthcare facility to one or more of the pre-existing patient records of at least the second healthcare facility for which a link has been identified;
define an initial level of assurance in the respective one or more links in response to identification of the one or more links, the initial level of assurance being based on a probabilistic analysis of the plurality of demographic attributes of the person and the demographic attributes of the patients associated with the pre-existing patient records;
in response to identification of the one or more links, provide information to the first healthcare facility visited by the person regarding the pre-existing patient records from at least the second healthcare facility for which a link has been identified with the patient record associated with the person and receive external information provided by the person at the first healthcare facility regarding a relationship between the person and the respective patients associated with the pre-existing patient records or regarding confirmation of an identity of the person;
define a level of assurance in the respective one or more links based upon the external information;
cause a network link to be established between the first and second healthcare facilities to permit at least portions of the patient records to be shared based upon the level of link assurance; and
following establishment of the network link, control actions taken based upon the level of assurance in the links to the respective patient records by permitting different actions to be taken with respect to the pre-existing patient records depending upon the level of assurance in the links to the respective patient records, wherein the health information computing device is configured to control actions taken based upon the level of assurance in the links by communicating, responsive to a request by the person for admission at the first health care facility, information from the pre-existing patient records regarding a prior encounter of the person but not documentation associated with the prior encounter from the second health care facility to the first health care facility in an instance in which the link has a first level of assurance and communicating, responsive to the request by the person for admission at the first health care facility, information from the pre-existing patient records regarding the prior encounter of the person as well as documentation associated with the prior encounter from the second health care facility to the first health care facility in an instance in which the link has a second level of assurance;

wherein the processing circuitry is further configured to define the level of assurance by re-defining the initial level of assurance in the respective one or more links based upon the external information.

15. A computing device according to claim 14 wherein the processing circuitry is configured to receive external information by receiving confirmation or denial from the person as to whether the person is the respective patient associated with a pre-existing record.

16. A computing device according to claim 14 wherein the processing circuitry is configured to receive external information by receiving confirmation of an identity of the person based upon an identification credential.

17. A computing device according to claim 14 wherein the processing circuitry is configured to receive external information by receiving confirmation of an identity of the person based upon biometric information.

18. A computer program product implemented by a health information infrastructure, comprising at least a computer device, and comprising a non-transitory computer readable storage medium having program code portions stored thereon, the program code portions configured, upon execution, to:

identify one or more links between a patient record associated with a person who has visited a first healthcare facility and pre-existing patient records from at least a second healthcare facility, wherein each pre-existing patient record has a plurality of demographic attributes associated with a patient, and wherein identifying one or more links comprises identifying one or more links based upon an analysis of demographic attributes of the person and the respective patients associated with the pre-existing patient records;

defining an initial level of assurance in the respective one or more links in response to identification of the one or more links, the initial level of assurance being based on a probabilistic analysis of the plurality of demographic attributes of the person and the demographic attributes of the patients associated with the pre-existing patient records access a record of each of a plurality of persons in a persons database and access patient records provided by respective healthcare facilities in one or more healthcare facility databases, wherein the patient records stored in one or more healthcare facility databases comprise at least a portion of corresponding patient records maintained by the respective healthcare facilities, and wherein identifying the one or more links comprises modifying the persons database to include a pointer from the record of the person who has visited the first healthcare facility to one or more of the pre-existing patient records of at least the second healthcare facility for which a link has been identified;

in response to identification of the one or more links, provide information to the first healthcare facility visited by the person regarding the pre-existing patient records from at least the second healthcare facility for which a link has been identified with the patient record associated with the person and receive external information provided by the person at the first healthcare facility regarding a relationship between the person and the respective patients associated with the pre-existing patient records or regarding confirmation of an identity of the person;

define a level of assurance in the respective one or more links based upon the external information;

cause a network link to be established between the first and second healthcare facilities to permit at least portions of the patient records to be shared based upon the level of link assurance; and following establishment of the network link, control actions taken based upon the level of assurance in the links to the respective patient records by permitting different actions to be taken with respect to the pre-existing patient records depending upon the level of assurance in the links to the respective patient records, wherein the program code portions are configured, upon execution, to control actions taken based upon the level of assurance in the links by communicating, responsive to a request by the person for admission at the first health care facility, information from the pre-existing patient records regarding a prior encounter of the person but not documentation associated with the prior encounter from the second health care facility to the first health care facility in an instance in which the link has a first level of assurance and communicating, responsive to the request by the person for admission at the first health care facility, information from the pre-existing patient records regarding the prior encounter of the person as well as documentation associated with the prior encounter from the second health care facility to the first health care facility in an instance in which the link has a second level of assurance;

wherein the program code portions are further configured to define the level of assurance by re-defining the initial level of assurance in the respective one or more links based upon the external information.

* * * * *

UNITED STATES PATENT AND TRADEMARK OFFICE
CERTIFICATE OF CORRECTION

| | |
|---|---|
| PATENT NO. | : 11,114,185 B1 |
| APPLICATION NO. | : 14/450883 |
| DATED | : September 7, 2021 |
| INVENTOR(S) | : Malec et al. |

It is certified that error appears in the above-identified patent and that said Letters Patent is hereby corrected as shown below:

In the Claims

Column 23, Line 49, Claim 18:
Please correct "records access a record"
To read -- records;
access a record --

Signed and Sealed this
Fifth Day of July, 2022

Katherine Kelly Vidal
*Director of the United States Patent and Trademark Office*